United States Patent
Rickerd et al.

(10) Patent No.: US 8,371,555 B2
(45) Date of Patent: Feb. 12, 2013

(54) SPLITTABLE HEMOSTASIS VALVE

(75) Inventors: Claude Rickerd, Bloomington, MN (US); Kirk Honour, Minnetonka, MN (US); Daniel J. Potter, Stillwater, MN (US)

(73) Assignee: Pacesetter, Inc., Sylmar, CA (US)

( * ) Notice: Subject to any disclaimer, the term of this patent is extended or adjusted under 35 U.S.C. 154(b) by 2251 days.

(21) Appl. No.: 11/029,800

(22) Filed: Jan. 4, 2005

(65) Prior Publication Data

US 2006/0145116 A1 Jul. 6, 2006

(51) Int. Cl.
*F16K 27/08* (2006.01)

(52) U.S. Cl. ............ 251/367; 604/167.04; 604/256

(58) Field of Classification Search .......... 251/367, 251/366; 137/375, 315.01, 15.18, 315.33, 137/15.19, 614.03; 604/256, 161, 167.04, 604/160; 403/331; 285/70
See application file for complete search history.

(56) References Cited

U.S. PATENT DOCUMENTS

| | | | |
|---|---|---|---|
| 331,998 A * | 12/1885 | Parsels | 285/67 |
| 4,327,770 A * | 5/1982 | Brown et al. | 137/614.05 |
| 4,997,424 A | 3/1991 | Little | |
| 5,041,095 A * | 8/1991 | Littrell | 604/167.04 |
| 5,125,904 A | 6/1992 | Lee | |
| 5,312,355 A | 5/1994 | Lee | |
| 6,159,198 A | 12/2000 | Gardeski et al. | |
| 6,497,681 B1 | 12/2002 | Brenner | |
| 6,623,460 B1 * | 9/2003 | Heck | 604/256 |
| 6,836,687 B2 | 12/2004 | Kelley et al. | |
| 6,966,896 B2 | 11/2005 | Kurth et al. | |
| 2001/0049499 A1 * | 12/2001 | Lui et al. | 604/164.05 |
| 2002/0010425 A1 * | 1/2002 | Guo et al. | 604/167.04 |
| 2004/0054330 A1 * | 3/2004 | Kurth et al. | 604/160 |

* cited by examiner

*Primary Examiner* — Stephen M Hepperle
*Assistant Examiner* — Andrew J Rost
(74) *Attorney, Agent, or Firm* — Polsinelli Shughart PC

(57) ABSTRACT

The present invention is a splittable multi-piece hemostasis valve that is held together in an assembled condition via a binder formed about the assembled valve. The binder may be a sleeve of thin polymer material shrink-wrapped about the valve. When the valve needs to be split in order to clear a medical device such as a pacemaker lead, the sleeve is split and the valve is disassembled.

8 Claims, 5 Drawing Sheets

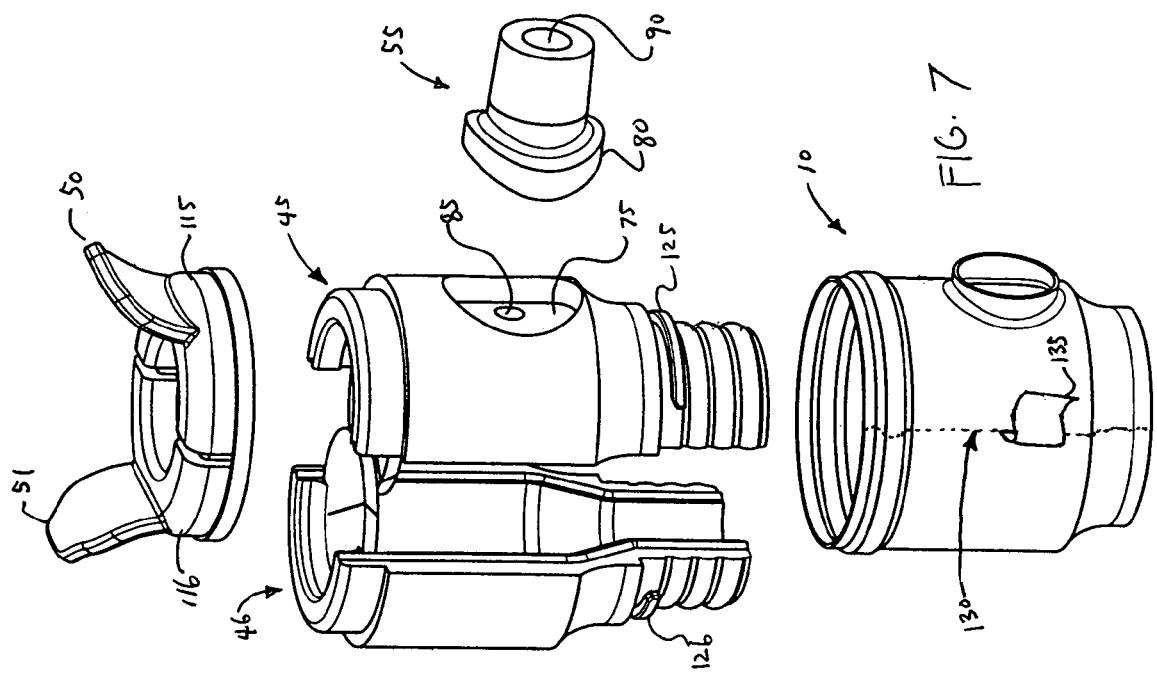
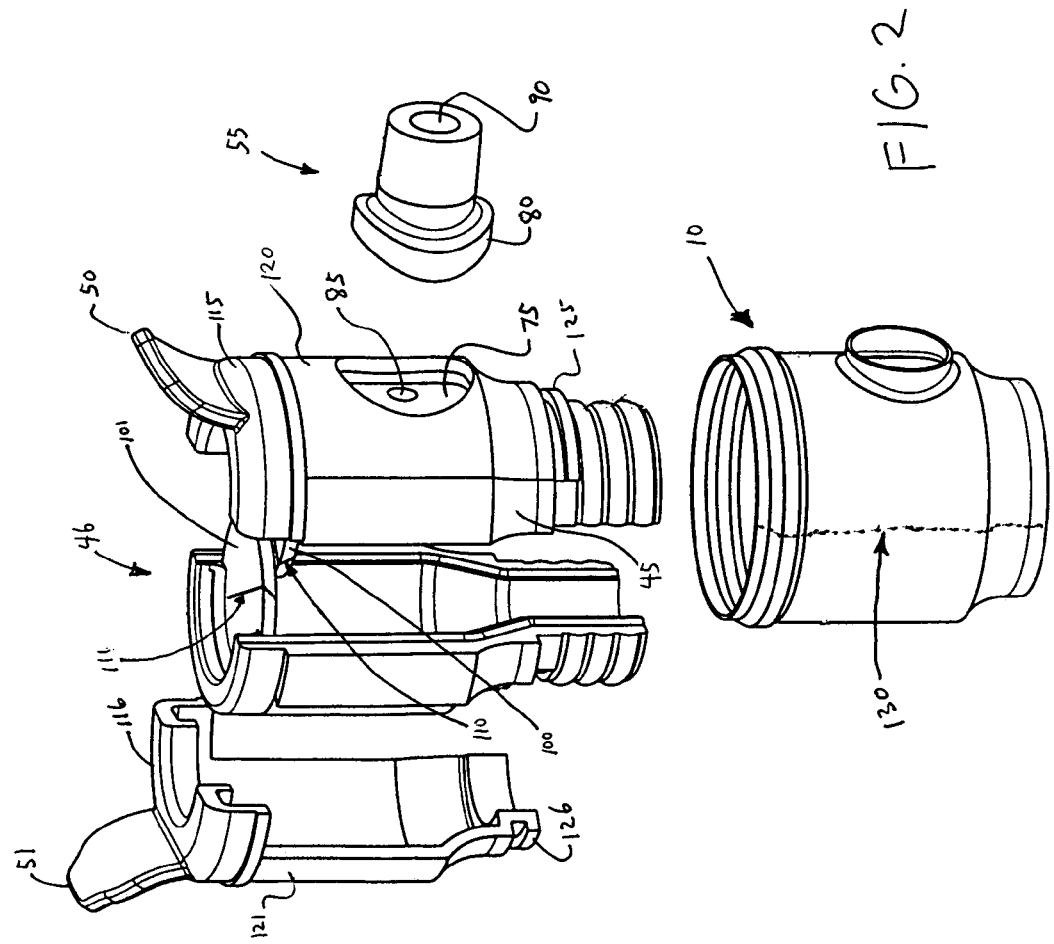

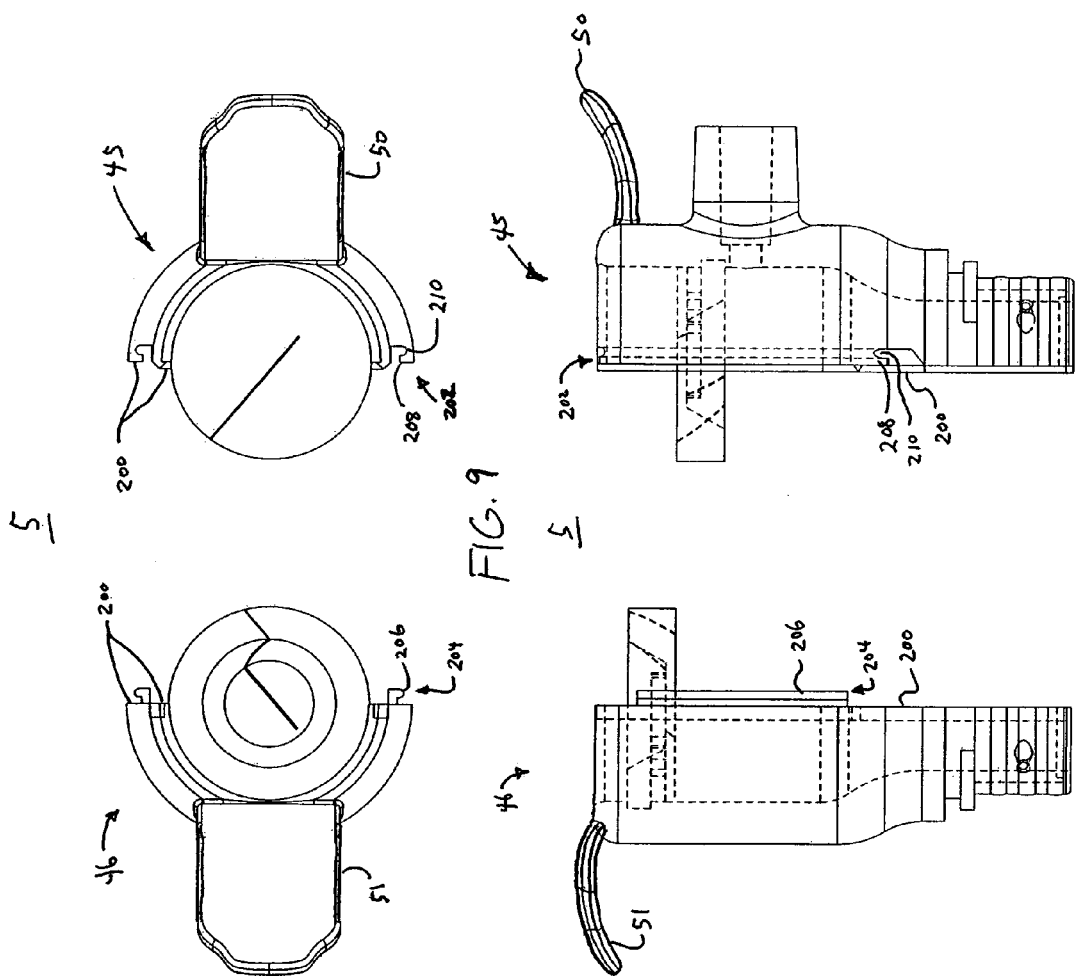

SPLITTABLE HEMOSTASIS VALVE

FIELD OF THE INVENTION

The present invention relates to hemostasis valves and methods of making and using such valves. More particularly, the present invention relates to splittable hemostasis valves and methods of making and using such valves.

BACKGROUND OF THE INVENTION

Splittable hemostasis valves are known in the art. However, these prior art valves have two disadvantages. First, the prior art valves can be overly difficult to split. Second, the prior art valves typically involve complex mold geometry and/or bonding methods such as sonic welding. Thus, the prior art valves are expensive to manufacture.

There is a need in the art for a splittable hemostasis valve that requires less effort to split and is less expensive to manufacture. There is also a need in the art for a method of manufacturing and a method of splitting such a valve.

BRIEF SUMMARY OF THE INVENTION

The present invention, in one embodiment, is a splittable hemostasis valve. The valve comprises a first valve wall, a second valve wall, and a binder. The first valve wall is mated together in an assembled condition with a second valve wall, thereby defining a chamber within the valve. The binder is routed around an outer surface of the walls and maintains the walls in the assembled condition.

In one embodiment, the binder is a thin layer of polymer shrink-wrapped about the outer surface of the valve walls. In one embodiment, the binder is adapted to fail at a specific location. For example, in one embodiment, the binder includes a scored or perforated line along which the binder will separate.

In one embodiment, the valve includes a mechanism for causing the binder to tear or split. In one embodiment, the mechanism is a first flange adjacent to the first valve wall and a second flange adjacent to the second valve wall, and forcing the flanges apart causes the binder to tear or split. In one embodiment, the mechanism is a pull-tab extending from the binder.

In one embodiment, the valve includes a first flexible membrane that extends between the valve walls. In another embodiment, the valve also includes a second flexible membrane that extends between the valve walls and is stacked on top of the first flexible membrane. In one embodiment, each flexible membrane includes a slit extending across a portion of the membrane. The slits radially offset from each other and intersect at a point along their lengths.

In one embodiment, the first valve wall includes a first integral flexible membrane that extends from the first valve wall to the second valve wall, and the first valve wall and the first flexible membrane are made from the same material. In another embodiment, the second valve wall also includes a second integral flexible membrane that extends from the second valve wall to the first valve wall and is stacked on top of the first flexible membrane. The second valve wall and the second flexible membrane are made from the same material. In one embodiment, each flexible membrane includes a slit that extends across a portion of the membrane, and the slits are radially offset and intersect at a point along their lengths.

In one embodiment, the valve includes a seat in the outer surface of the first valve wall. The seat is adapted to receive a tap and includes a hole through the first valve wall. The hole is for placing an internal chamber defined by the first and second valve walls in fluid communication with a bore through the tap.

The present invention, in one embodiment, is a method of manufacturing a splittable hemostasis valve. The method comprises mating a first valve wall with a second valve wall such that the valve walls define an interior chamber of the valve. A binder is then wrapped about an outer surface of the valve walls to maintain the valve walls in a mated condition.

The present invention, in one embodiment, is a method of splitting a splittable hemostasis valve to allow the removal of a medical device from within the valve. The method comprises splitting or tearing a binder that is wrapped around an outer surface of two valve walls that are held in an assembled condition by the binder. The split or torn binder is then removed from the outer surface of the valve walls, and the valve walls are disassembled from each other.

In one embodiment, a pair of flanges is spread apart in order to split or tear the binder. In one embodiment, a tab that extends from, or is otherwise coupled with, the binder is pulled to split or tear the binder.

In one embodiment, a portion of a flexible membrane between an end of a slit in the membrane and an edge of the membrane is torn to allow the medical device to pass through the edge of the membrane. In one embodiment, the medical device is passed through the edge of a membrane via a slit in the membrane that extends to the edge of the membrane.

The present invention, in one embodiment, is a splittable hemostasis valve. The valve comprises a first valve wall, a second valve wall, a first membrane, and a second membrane. The first valve wall is mated together in an assembled condition with the second valve wall. The first membrane extends between the first and second valve walls and includes a planar surface. The second membrane extends between the first and second valve walls and includes a planar surface abutted against the planar surface of the first membrane.

In one embodiment, the first membrane includes a conical surface opposite the planar surface of the first membrane, and the second membrane includes a conical surface opposite the planar surface of the second membrane. In one embodiment, the first membrane includes a slit that passes through the first membrane at an angle that is approximately 45 degrees from being perpendicular to the planar surface. In one embodiment, the first and second membranes each include a slit and the slits are radially offset from each other.

The present invention, in one embodiment, is a splittable hemostasis valve. The valve comprises a first valve wall mated together in an assembled condition with a second valve wall via a mechanically coupled separation joint. In one embodiment, the mechanically coupled separation joint includes a male structure on an end face of the first valve wall and a female structure on an end face of the second valve wall for receiving the male structure.

In one embodiment, the mechanically coupled separation joint is formed by press-fitting the first valve wall into engagement with the second valve wall. In one embodiment, the mechanically coupled separation joint is separated by sliding the first and second valve walls in directions that are opposite to each other and parallel to the mechanically coupled separation joint.

In one embodiment, each valve wall includes a flange that is oriented generally perpendicular to the mechanically coupled separation joint. In one embodiment, one flange is curved upward and the other flange is curved downward.

The present invention, in one embodiment, is a splittable hemostasis valve for coupling to a splittable catheter or sheath. The valve includes a first valve wall, a second valve wall, a feature for maintaining the valve walls in an assembled condition, and a membrane. The first valve wall includes an end adapted to couple to the catheter or sheath. The end includes an integral sealing ring extending along an outer circumferential surface of said end. The second valve wall includes an end adapted to couple to the catheter or sheath. The end includes an integral sealing ring extending along an outer circumferential surface of said end. The membrane extends between the valve walls. The membrane, sealing rings and at least a portion of the valve walls are formed from the same resilient material.

In one embodiment, the feature for maintaining the valve walls in an assembled condition is a binder extending about an outer circumferential surface of the valve walls. In another embodiment, the feature for maintaining the valve walls in an assembled condition is a mechanically coupled joint.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 2 is an exploded isometric view of the valve depicted in FIG. 1.

FIG. 7 is an exploded isometric view of another embodiment of the valve.

FIG. 8 is an elevation of the valve wherein the valve walls are decoupled from each other.

FIG. 9 is a top plan view of the valve wherein the valve walls are decoupled from each other.

DETAILED DESCRIPTION

Figure 1:
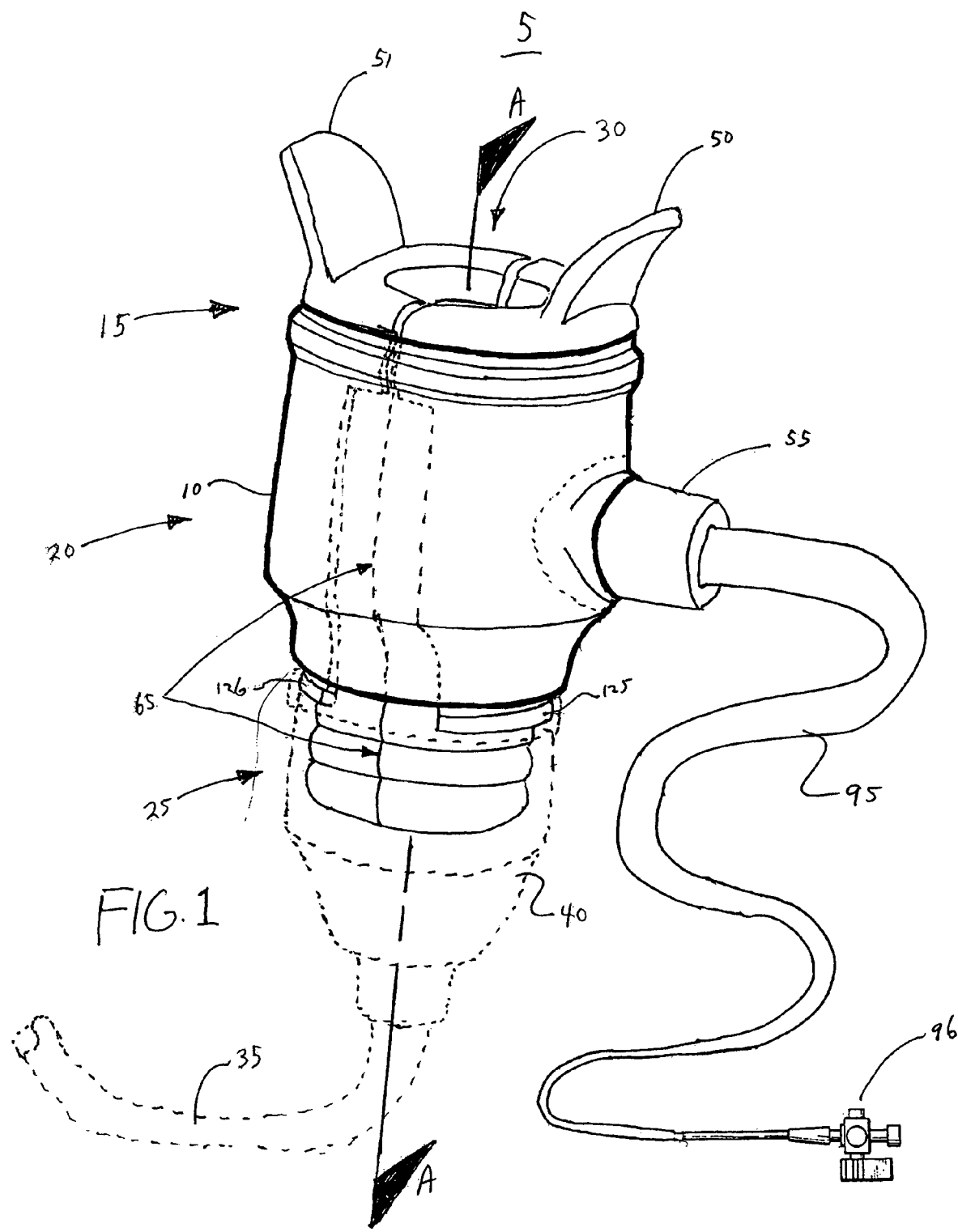
FIG. 1 is an isometric view of one embodiment of the present invention, which is a splittable multi-piece hemostasis valve

FIG. 1 is an isometric view of one embodiment of the present invention, which is a splittable multi-piece hemostasis valve 5 that is held together in an assembled condition via a sleeve 10 formed about the assembled valve 5. In one embodiment, the sleeve 10 is a thin polymer material shrink-wrapped about the valve 5. When the valve 5 needs to be split in order to clear a device (e.g., a pacemaker lead or other medical device), the sleeve 10 is split and the valve 5 is disassembled.

The valve 5 is advantageous for multiple reasons. First, because the valve 5 is assembled from multiple pieces and then shrink-wrapped together, it offers reduced manufacturing costs as compared to prior art splittable hemostasis valves. Second, the valve requires less effort to split than prior art splittable hemostasis valves.

As shown in FIG. 1, the valve 5 includes an entry end 15, a generally cylindrical body portion 20, and an attachment end 25. The entry end 15 has an opening 30 for receiving a catheter or other similar tubular medical device. The attachment end 25 is adapted to connect to a sheath 35 via a connector 40, both of which are shown in phantom in FIG. 1.

Figure 4:
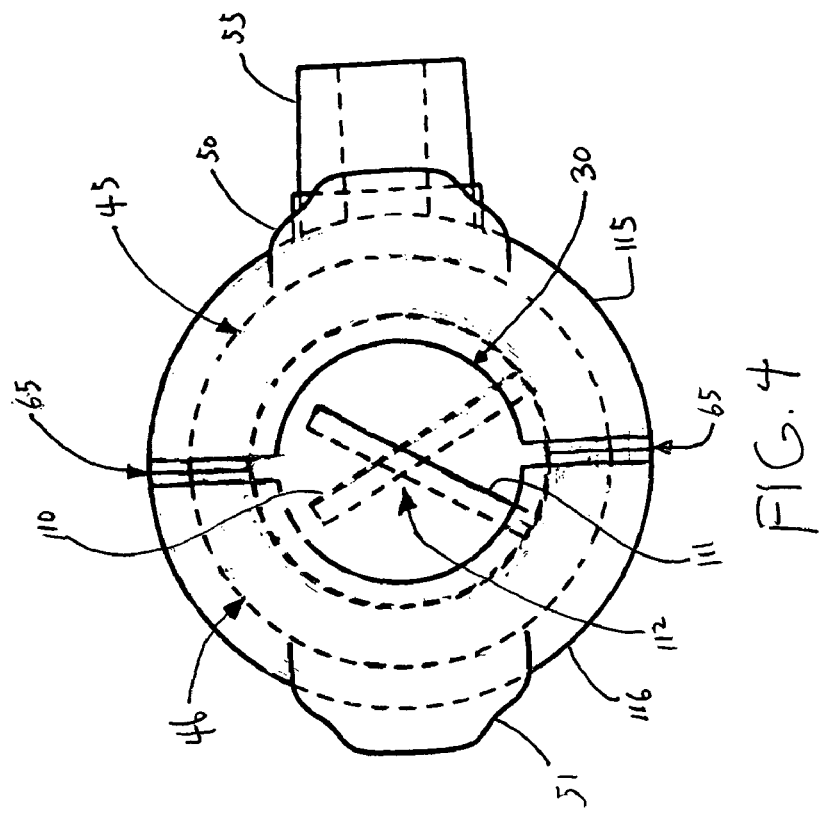
FIG. 4 is a top view of the assembled valve depicted in FIG. 1.
Figure 3:
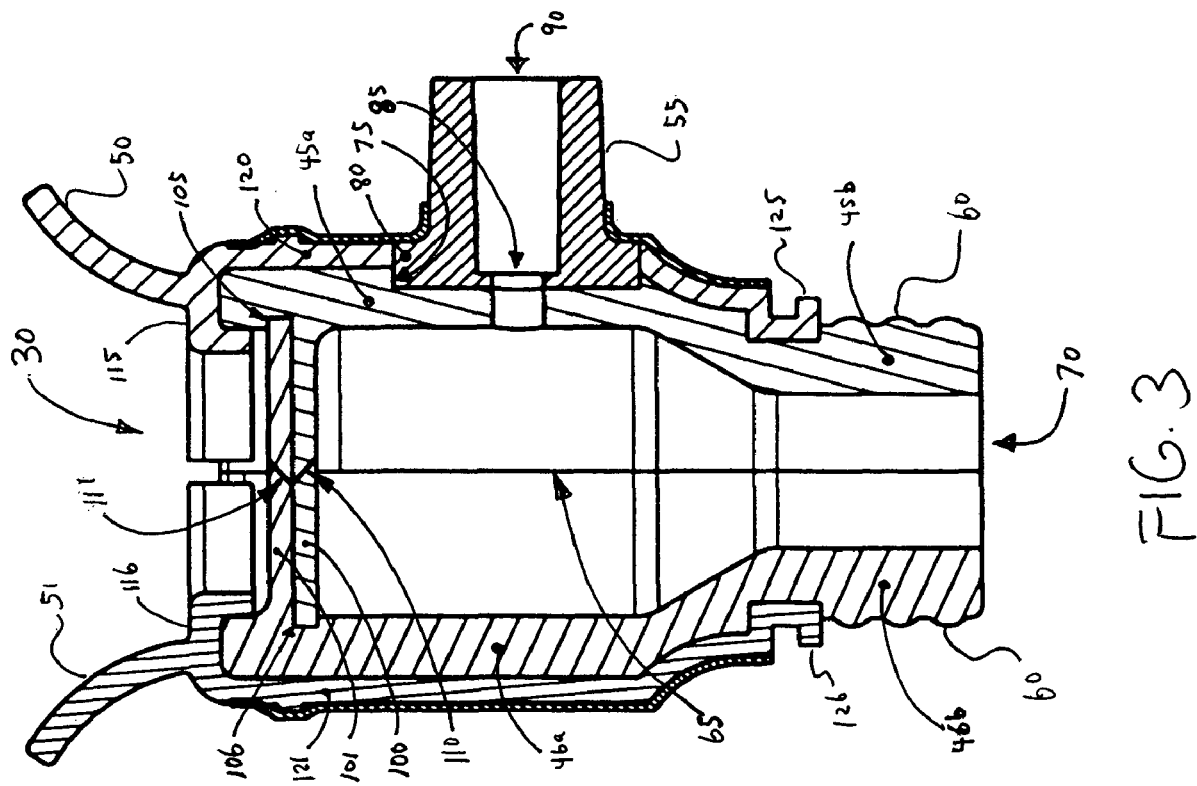
FIG. 3 is a cross-section elevation taken along section line AA in FIG. 1.

For a detailed description of the pieces comprising the splittable multi-piece hemostasis valve 5, reference is now made to FIGS. 2, 3 and 4. FIG. 2 is an exploded isometric view of the valve 5 depicted in FIG. 1. FIG. 3 is a cross-section elevation taken along section line AA in FIG. 1. FIG. 4 is a top view of the assembled valve 5 depicted in FIG. 1.

As shown in FIG. 2, the valve 5 is formed from multiple separate pieces. In one embodiment, the multiple separate pieces are right and left valve walls 45, 46, right and left flanges 50, 51, a tap 55 and the sleeve 10.

As shown in FIG. 2 and FIG. 3, in one embodiment, each valve wall 45, 46 has a body portion 45a, 46a and an attachment portion 45b, 46b. The body portions 45a, 46a taper as they transition into the attachment portions 45b, 46b. Each attachment portion has sealing rings 60 about its outer circumference.

In one embodiment, each valve wall 45, 46 is formed from a generally rigid, hard material (e.g., acrylonitrile-butadiene-styrene "ABS", polyether block amides "PEBAX", high density polyethylene "HDPE", polycarbonate, nylon, etc.). Where the valve walls 45, 46 are formed from such a generally rigid, hard material, the sealing rings 60 will be formed from a generally resilient, soft material (e.g., silicone, polyether block amides "PEBAX", poly biphenyl compounds "PBC", santaprene, neoprene, latex, etc.) that is separately applied to the attachment portions 45b, 46b.

In another embodiment, each valve wall 45, 46 is formed from a generally resilient, soft material (e.g., silicone, polyether block amides "PEBAX", poly biphenyl compounds "PBC", santaprene, neoprene, latex, etc.). Where the valve walls 45, 46 are formed from such a generally resilient, soft material, the sealing rings 60 are integral to the attachment portions 45b, 46b.

Figure 5:
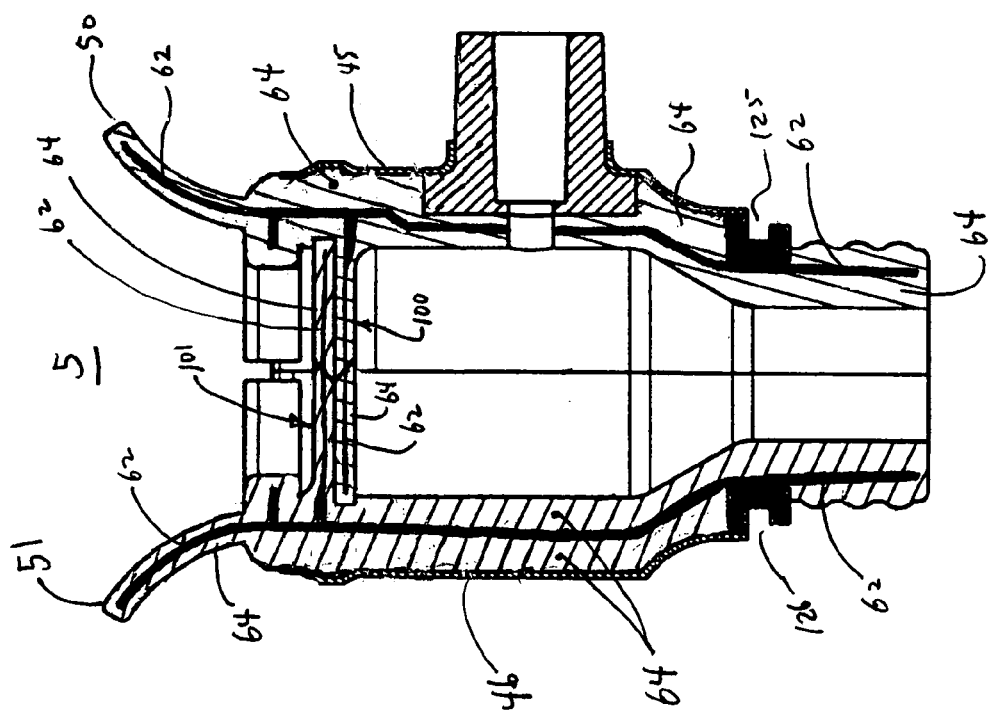
FIG. 5 is a cross-section elevation taken along section line AA in FIG. 1.

In one embodiment, as indicated in FIG. 5, which is a cross-section elevation taken along section line AA in FIG. 1, each valve wall 45, 46 (including, in one embodiment, the respective flanges 50, 51, flexible membranes and other features of each valve wall) is a sandwich of materials. For example, each valve wall 45, 46 has an interior supportive structure (i.e., an endoskeleton 62) formed from a generally rigid, hard material (e.g., acrylonitrile-butadiene-styrene "ABS", polyether block amides "PEBAX", high density polyethylene "HDPE", polycarbonate, nylon, etc.). The endoskeleton 62 of each valve wall 45, 46 forms and maintains the general shape of each valve wall 45, 46. The endoskeleton 62 is covered by a layer 64 of generally resilient, soft material (e.g., silicone, polyether block amides "PEBAX", poly biphenyl compounds "PBC", santaprene, neoprene, latex, etc.) that provides, and defines, the surfaces of the valve 5.

As can be understood from FIGS. 2, 3 and 4, in one embodiment, each valve wall 45, 46 (shown in FIG. 4 by hidden lines) is semicircular. Thus, when the right semicircular valve wall 45 is mated with the left semicircular valve wall 46 to form the assembled valve 5 as shown in FIGS. 1, 3 and 4, a separation joint 65 forms between the two semicircular valve walls 45, 46, and a generally cylindrical interior chamber 70 is defined by the valve walls 45, 46.

As illustrated in FIGS. 1 and 3, in one embodiment, the exterior surface of the body portion 45a of the right valve wall 45 has a recessed seat 75 for receiving the base 80 of the tap 55. A hole 85 is generally centered in the seat 75 and passes through the right valve wall 45 to place the interior chamber 70 in fluid communication with a bore 90 passing through the tap 55. As indicated in FIG. 1, a flexible tube 95 runs from the bore 90 to a two-way shut-off valve 96.

In one embodiment, the tap 55 is formed from a generally rigid, hard material (e.g., acrylonitrile-butadiene-styrene "ABS", polyether block amides "PEBAX", high density polyethylene "HDPE", polycarbonate, nylon, etc.). In another embodiment, the tap 55 is formed from a generally resilient, soft material (e.g., silicone, polyether block amides "PEBAX", poly biphenyl compounds "PBC", santaprene, neoprene, latex, etc.).

As shown in FIGS. 2, 3 and 4, each valve wall 45, 46 has a flexible membrane 100, 101 and a groove ring 105, 106. Each membrane 100, 101 extends across the opening 30 in the entry end 15 of the valve 5 from its respective valve wall 45, 46 and seats in the groove ring 105, 106 of the opposite valve wall 45, 46. As illustrated in FIG. 3, in one embodiment, each membrane 100, 101 has an upper and lower generally planar surface. Thus, in one embodiment, each membrane 100, 101 is a generally planar disc. As shown in FIG. 3, the adjacent planar surfaces of the membranes 100, 101 abut such that the one membrane 101 is stacked on the other membrane 100.

As indicated in FIGS. 2, 3 and 4, each flexible membrane 100, 101 includes a slit 110, 111 running from or near one side of the membrane 100, 101 towards the opposite side of the membrane 100, 101. As shown in FIG. 4, the slits 110, 111 are radially offset from each other such that they crisscross to form an intersection 112.

Figure 6:
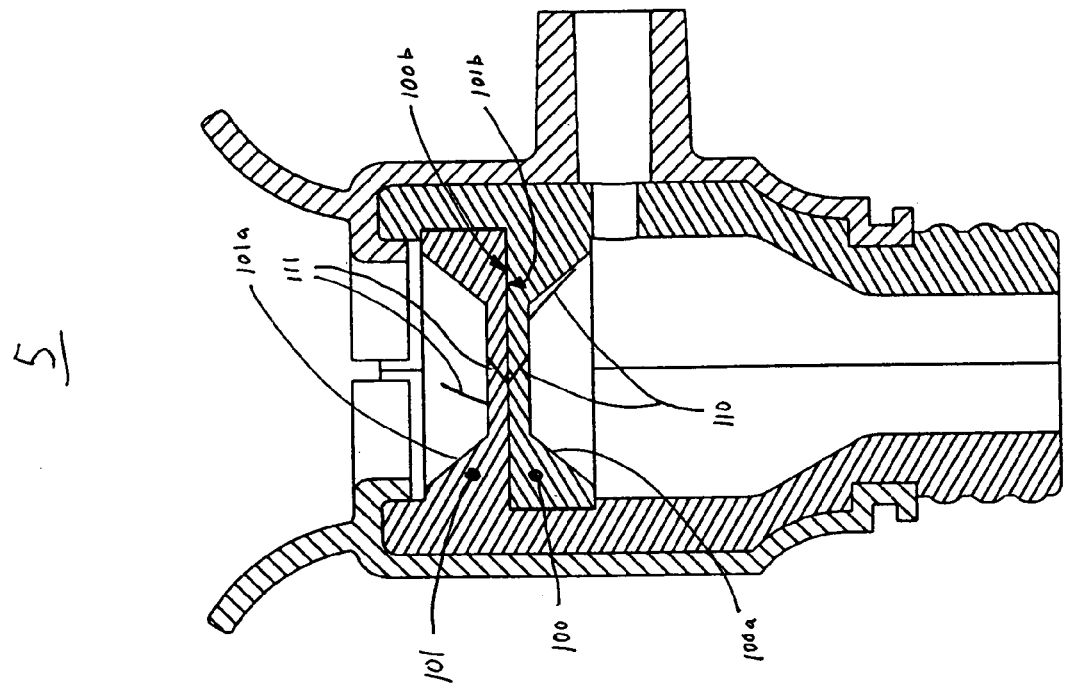
FIG. 6 is a cross-section elevation taken along section line AA in FIG. 1.

As indicated in FIG. 6, which is a cross-section elevation taken along section line AA in FIG. 1, in one embodiment, each membrane 100, 101 has a generally conical side 100a, 101a and a generally planar side 100b, 101b. As shown in FIG. 6, in one embodiment, the membranes 100, 101 are arranged such that one membrane 101 is stacked on the other membrane 100 with the planar sides 100b, 101b abutting each other and the conical sides 100a, 101a facing away from each other. Each membrane 100, 101 includes a slit 110, 111 as previously described. Again, in one embodiment, the slits 110, 111 are radially offset from each other. In one embodiment, each slit 110, 111 passes through it respective membrane 100, 101 at an angle that is approximately 45 degrees from being perpendicular to the membrane's planar face 100b, 101b.

In one embodiment, where the valve walls 45, 46 are formed from a generally rigid, hard material as discussed above, each flexible membrane 100, 101 will be formed from a generally resilient, soft material (e.g., silicone, polyether block amides "PEBAX", poly biphenyl compounds "PBC", santaprene, neoprene, latex, etc.) and applied separately to reside in a groove ring in its respective valve wall 45, 46. In another embodiment, where the valve walls 45, 46 are formed from a generally resilient, soft material as discussed above, each flexible membrane 100, 101 will be integrally formed with its respective valve wall 45, 46. In another embodiment, the flexible membranes 100, 101 have an endoskeleton 62 with a layer 64 formed over the endoskeleton 62 as discussed above in reference to FIG. 5.

As shown in FIGS. 2 and 3, in one embodiment, each flange 50, 51 extends from a collar 115, 116 that is adjacent to, and generally defines, the opening 30 at the entry end 10. In one embodiment, a flange side 120, 121 extends from each collar 115, 116 along the exterior surfaces of the valve walls 45, 46, and the right flange side includes and an opening 122 that coincides with the seat 75 for receiving the base 80 of the tap 55. In one embodiment each flange side 45, 46 includes a bayonet-type lock element 125, 126 for locking the valve 5 to the connector 40 as illustrated in FIG. 1.

In one embodiment, the flanges 50, 51, collars 115, 116 and the flange sides 120, 121 are formed from a generally rigid, hard material (e.g., acrylonitrile-butadiene-styrene "ABS", polyether block amides "PEBAX", high density polyethylene "HDPE", polycarbonate, nylon, etc.). In one embodiment, where the valve walls 45, 46 are formed from a generally rigid, hard material as discussed above, the flanges 50, 51, collars 115, 116 and the flange sides 120, 121 may be integrally formed with the valve walls 45, 46.

As indicated in FIG. 7, which is an exploded isometric view of another embodiment of the valve 5, each flange 50, 51 extends from a collar 115, 116, but no collar 115, 116 has a flange side 120, 121 extending therefrom. In such an embodiment, the bayonet-type lock elements 125, 126 are integrally formed with the attachment portions 45b, 46b of the valve walls 45, 46. In one embodiment, the bayonet-type lock elements 125, 126 are exposed extensions of the endoskeleton 62 discussed above in reference to FIG. 5.

In one embodiment, the flanges 50, 51 and collars 115, 116 are formed from a generally rigid, hard material (e.g., acrylonitrile-butadiene-styrene "ABS", polyether block amides "PEBAX", high density polyethylene "HDPE", polycarbonate, nylon, etc.). In one embodiment, where the valve walls 45, 46 are formed from a generally rigid, hard material as discussed above, the flanges 50, 51 and collars 115, 116 may be integrally formed with their respective valve walls 45, 46. In one embodiment, the flanges 50, 51 have an endoskeleton 62 with a layer 64 formed over the endoskeleton 62 as discussed above in reference to FIG. 5.

As shown in FIGS. 1-3, in one embodiment, once the valve 5 is assembled, a binder or binding system 10 is used to maintain the valve 5 in the assembled state by routing the binding system 10 about the outer circumferential surface of the valve's body portion 20. In one embodiment, the binding system 10 is a sleeve 10 formed from a thin layer of material (e.g., a polymer) that is heat-shrunk about the valve's body portion 20. In another embodiment, the binding system 10 is a sleeve 10 formed from a thin layer of material that is wrapped around the valve's body portion 20 and secured with an adhesive. In another embodiment, the binding system 10 is a sleeve 10 formed from a thin layer of elastic material that is slipped over one end of the valve 5 and onto the valve's body portion 20. In one embodiment, the binding system 10 is one or more bands or rings of material routed about the outer circumferential surface of the valve's body portion 20. In such an embodiment, the bands or rings may be rigid or elastic. The bands or rings may be secured about the valve's body portion 20 via heat-shrinking or an adhesive.

As illustrated in FIGS. 2 and 7, in one embodiment, the binder or binding system 10 is adapted to be removable from the valve 5 in order to allow the valve 5 to be disassembled. In one embodiment, where the binding system 10 is secured to the valve 5 via an adhesive, the binding system 10 may be pealed away from the valve 5 to allow the valve 5 to be disassembled. In one embodiment, where the binding system is a sleeve 10 that has been heat-shrunk about the valve 5, the sleeve 10 may be split or cut. For example, a physician may cut the sleeve 10 with a scalpel and pull the sleeve 10 away from the valve 5 to allow the valve 5 to be disassembled. Alternatively, the physician may force the flanges 50, 51 apart to cause the sleeve 10 to split, thereby allowing the sleeve 10 to be removed and the valve 5 to be disassembled.

As shown in FIG. 7, in one embodiment, the sleeve 10 is provided with a wing or tab 135 that may be grasped and used to cause the sleeve 10 to peel, tear or split away from the valve 5. In one embodiment, because the sleeve 10 is equipped with the wing or tab 135, the flanges 50, 51 are not required in order to cause the sleeve 10 to split or tear. As a result, the flanges 50, 51 are not provided.

In one embodiment, a binder or binding system 10, such as a sleeve 10, band or ring, may be adapted to fail at a specific point along its circumferential surface. For example, as indicated in FIGS. 2 and 7, the sleeve 10 may have a scored or perforated line 130 that allows the sleeve to fail along the line's length when the valve walls 45, 46 or flanges 50, 51 are sufficiently forced apart.

For a discussion of an embodiment of the valve 5 wherein the above discussed binder 10 has been replaced with mechanical coupling seams for coupling the two valve walls 45, 46 together, reference is now made to FIGS. 8 and 9. FIG. 8 is an elevation of the valve 5 wherein the valve walls 45, 46 are decoupled from each other. FIG. 9 is a top plan view of the valve 5 wherein the valve walls 45, 46 are decoupled from each other.

As indicated in FIGS. 8 and 9, the valve walls 45, 46 are generally the same as those previously described, except with respect the to orientation of the flanges 50, 51 and the arrangement utilized to couple the valve walls 45, 46 together. For example, as shown in FIGS. 8 and 9, in one embodiment, the end faces 200 of each valve wall 45, 46, which abut to form the separation joints 65 (see FIG. 1), have features or structures 202, 204 that engage with each other to form mechanically coupled separation joints.

As illustrated in FIGS. 8 and 9, in one embodiment, each end face 200 of the right valve wall 45 is equipped with a female feature or structure 202 for receiving and mechanically coupling with a male feature or structure 204 of the corresponding end face 200 of the left valve wall 46. In one embodiment, the end faces 200 of the left valve wall 46 are equipped with female structures 202, and the end faces 200 of the right valve wall 45 are equipped with male structures 204. In one embodiment, one end face 200 of the left valve wall 46 will have a female structure 202 and the other end face 200 will have a male structure 204. Similarly, in the same embodiment, the right valve wall 45 have female and male structures 202, 204 that correspond to those on the left valve wall 46.

As shown in FIGS. 8 and 9, in one embodiment, each male structure 204 includes a ridge 206 running the length of the male structure 204. Each female structure 202 includes a lip 208 that helps to define a groove 210. Each lip 208 and groove 210 run the length of the respective female structure 202.

As can be understood from FIG. 9, in one embodiment, the mechanically coupled separation joints are formed by press-fitting together the end faces 200 of the valve walls 45, 46. For example, when the male structures 204 are inserted into the corresponding female structures 202, the lip 208 of each female structure 202 deflects to allow sufficient space for the ridge 206 to pass the lip 208 and be received in the groove 210. Once the ridge 206 has cleared the lip 208, the lip 208 returns to its non-deflected configuration to hold the ridge 206 within the groove 210.

In one embodiment, to split the valve 5 and separate the valve walls 45, 46 from each other, a user simply forces the flanges 50, 51 apart as if attempting to split a binder 10, as previously described in reference to FIGS. 2 and 7. This causes the lips 208 to deflect as necessary to allow the ridges 206 to escape their corresponding grooves 210.

In another embodiment, as can be understood from FIGS. 8 and 9, the valve walls 45, 46 are displaced oppositely along the separation joint 65 (see FIG. 1). In other words, a user forces the flanges 50, 51 oppositely from each other in directions that are parallel to the separation joints 65 of the valve 5. This causes the valve walls 45, 46 to displace oppositely such that their respective end faces 200 slideably displace against each other in opposite directions. This allows the ridge 206 of each male structure 204 to slide out of the groove 210 of the respective female structure 202. Once the ridges 206 are free of their respective grooves 210, the valve walls 45, 46 may be separated.

In one embodiment, the aforementioned process is reversed to join the valve walls 45, 46 together. In other words, the ridges 206 are slid into their respective grooves 210 until the bottom and top ends of the right valve wall 45 align with the corresponding ends of the left valve wall 46.

In one embodiment, as shown in FIGS. 8 and 9, the flanges 50, 51 are configured to facilitate the sliding of one valve wall 45 relative to the other valve wall 46. For example, in one embodiment, the flanges 50, 51 extend generally perpendicularly to the end faces 200 of their respective valve walls 45, 46. In one embodiment, the right flange 50 is slightly curved downward to ergonomically receive the user's downward pressing finger, and the left flange 51 is slightly curved upward to ergonomically receive the user's upward pressing finger.

In one embodiment, the end faces 200 and female and male structures 202, 204 are formed from a generally rigid, hard material (e.g., acrylonitrile-butadiene-styrene "ABS", polyether block amides "PEBAX", high density polyethylene "HDPE", polycarbonate, nylon, etc.). In another embodiment, the end faces 200 and female and male structures 202, 204 are formed from a generally resilient, soft material (e.g., silicone, polyether block amides "PEBAX", poly biphenyl compounds "PBC", santaprene, neoprene, latex, etc.).

In one embodiment, the end faces 200 and structures 202, 204 of one of the valve walls 45, 46 are formed from one of the aforementioned generally resilient, soft materials, and the end faces 200 and structures 202, 204 of the other valve wall 45, 46 are formed from one of the aforementioned generally rigid, hard materials. In one embodiment, end faces 200 are formed from one of the aforementioned generally resilient, soft materials, and the female and male structures 202, 204 are formed from one of the aforementioned generally rigid, hard materials. For example, in one embodiment, the female and male structures 202, 204 are an exposed part of the generally rigid, hard endoskeleton 62 and the end faces 200 are a generally resilient, soft layer 64 formed over the endoskeleton 62, as discussed above in reference to FIG. 5.

A method of utilizing the valve 5 is now provided while referring to FIGS. 1-4 and 7. A valve 5 is provided in the assembled configuration shown in FIG. 1. The attachment end 25 of the valve 5 is inserted into the connector 40 and the bayonet-type lock elements 125, 126 are engaged with their counterparts in the connector 40 to secure the valve 5 to the connector 40 and the sheath 35 extending therefrom. The sheath 35 is introduced into a body lumen of a patient via means well known in the art.

Once the sheath 35 is positioned properly within the patient, a catheter (or guidewire) is then inserted through the opening 30, the slits 110, 111 in the membranes 100, 101, the internal chamber 70, and into the sheath 35. The membranes 100, 101 seal fluidly tight about the catheter to prevent blood from leaking out of the valve's opening 30. After the catheter procedure is completed, the catheter is withdrawn from the sheath 35 and the valve 5, and the membranes 100, 101 reseal to prevent blood leakage.

A pacemaker lead is then inserted through the membranes 100, 101 of the valve 5 and into the sheath 35. The distal ends of the pacemaker leads are implanted within the patient. The sheath 35 is then removed from the patient while leaving the pacemaker leads in place. However, to allow the sheath 35 to clear the proximal ends of the pacemaker leads, the valve 5 and the sheath 35 must be split. At this time, the physician splits the valve's binding system 10 to facilitate the disassembly of the valve 5. In one embodiment, the physician places his thumbs on the flanges 50, 51 and sufficiently forces them apart to cause the sleeve 10 to split at the perforated line 130. The split sleeve 10 is then removed from the valve 5 and the valve 5 is disassembled into right and left sections as indicated in FIG. 2. At this time, the pacemaker lead is removed from the slits 110, 111 in the membranes 100, 101.

To remove the pacemaker lead from the slits 110, 111 of the membranes 100, 101, the pacemaker lead is moved along the slits 110, 111 towards a location on each membrane 100, 101 where each slit 110, 111 intersects or nearly intersects the edge of the membrane 100, 101. Once the pacemaker lead has reached the edge of the membrane 100, 101, the pacemaker lead can be removed from the slit 110, 111.

Where the slit 110, 111 does not quite reach the edge of the membrane 100, 101, the last remaining edge portion of the membrane 100, 101 between the end of the slit 110, 111 and the edge of the membrane 100, 101 is simply torn or cut to extend the slit 110, 111 to the edge and allow the pacemaker lead to pass through the membrane edge portion. The proximal ends of the pacemaker leads may now be cleared and, as a result, the sheath 35 may be removed from the patient.

Although the present invention has been described with reference to preferred embodiments, persons skilled in the art will recognize that changes may be made in form and detail without departing from the spirit and scope of the invention.

We claim:

1. A splittable hemostasis valve comprising a first valve wall mated together in an assembled condition with a second valve wall via a mechanically coupled separation joint, wherein the mechanically coupled separation joint is separated by sliding the first and second valve walls in directions that are opposite to each other and parallel to a longitudinal axis of the splittable hemostasis valve.

2. The valve of claim 1, wherein each valve wall includes a flange that is oriented generally perpendicular to the mechanically coupled separation joint.

3. The valve of claim 2, wherein one flange is curved upward and the other flange is curved downward.

4. The valve of claim 1, further comprising a first membrane extending between the first and second valve walls and including a planar surface; and a second membrane extending between the first and second valve walls and including a planar surface abutted against the planar surface of the first membrane.

5. The valve of claim 4, wherein the first membrane includes a conical surface opposite the planar surface of the first membrane.

6. The valve of claim 5, wherein the second membrane includes a conical surface opposite the planar surface of the second membrane.

7. The valve of claim 4, wherein the first membrane includes a slit that passes through the first membrane at an angle that is approximately 45 degrees from being perpendicular to the planar surface.

8. The valve of claim 4, wherein the first and second membranes each include a slit and the slits are radially offset from each other.

* * * * *